(12) United States Patent
Nord et al.

(10) Patent No.: US 9,138,598 B2
(45) Date of Patent: *Sep. 22, 2015

(54) METHOD AND APPARATUS PERTAINING TO OPTIMIZING A RADIATION-TREATMENT LEAF-SEQUENCE PLAN

(71) Applicant: Varian Medical Systems International AG, Cham (CH)

(72) Inventors: Janne Nord, Espoo (FI); Jarkko Peltola, Tuusula (FI)

(73) Assignee: Varian Medical Systems International AG, Cham (CH)

( * ) Notice: Subject to any disclaimer, the term of this patent is extended or adjusted under 35 U.S.C. 154(b) by 230 days.

This patent is subject to a terminal disclaimer.

(21) Appl. No.: 13/630,374

(22) Filed: Sep. 28, 2012

(65) Prior Publication Data
US 2013/0023718 A1  Jan. 24, 2013

Related U.S. Application Data

(63) Continuation of application No. 12/879,165, filed on Sep. 10, 2010, now Pat. No. 8,295,436.

(51) Int. Cl.
*A61N 5/10* (2006.01)

(52) U.S. Cl.
CPC .................... *A61N 5/1036* (2013.01)

(58) Field of Classification Search
CPC ............ A61N 5/1036; A61N 5/1045
USPC ............................................. 378/65
See application file for complete search history.

(56) References Cited

U.S. PATENT DOCUMENTS

| 6,052,430 | A | 4/2000 | Siochi et al. |
|---|---|---|---|
| 6,999,556 | B2 | 2/2006 | Nakano |
| 7,469,035 | B2 | 12/2008 | Keall et al. |
| 7,609,810 | B2 | 10/2009 | Yi et al. |
| 8,295,436 | B2 | 10/2012 | Nord et al. |
| 2009/0041188 | A1* | 2/2009 | Keall et al. ............ 378/65 |

* cited by examiner

*Primary Examiner* — Glen Kao
(74) *Attorney, Agent, or Firm* — Fitch, Even, Tabin & Flannery LLP

(57) ABSTRACT

Determine first information regarding physical-movement limitations pertaining to at least one multi-leaf collimator and also determine second information regarding movement of the treatment target with respect to the given patient. Then, while optimizing a radiation-treatment leaf-sequence plan, constrain individually-planned leaf positions as a function, at least in part, of the first information, the second information, and planned positions of adjacent leaves. By one approach, the first information can comprise information regarding a speed (such as a maximum speed) at which individual leaves of the multi-leaf collimator are able to move during a treatment session. By one approach, the second information can comprise information regarding a distance (such as a maximum distance) that one or more parts of the treatment target may possibly move as compared to a presumed position used during the optimizing of the radiation-treatment leaf-sequence plan.

10 Claims, 5 Drawing Sheets

METHOD AND APPARATUS PERTAINING TO OPTIMIZING A RADIATION-TREATMENT LEAF-SEQUENCE PLAN

RELATED APPLICATION(S)

This is a continuation of U.S. patent application Ser. No. 12/879,165, Filed Sep. 10, 2010, entitled METHOD AND APPARATUS PERTAINING TO OPTIMIZING A RADIATION-TREATMENT LEAF-SEQUENCE PLAN, which is incorporated by reference in its entirety herein.

This application is related to co-pending and co-owned U.S. patent application Ser. No. 12/837,123, entitled METHOD AND APPARATUS PERTAINING TO USE OF JAWS DURING RADIATION TREATMENT and filed Jul. 15, 2010, which is incorporated by reference in its entirety herein.

This application is also related to co-pending and co-owned U.S. patent application Ser. No. 12/860,466, entitled APPARATUS AND METHOD PERTAINING TO RADIATION-TREATMENT PLANNING OPTIMIZATION and filed Aug. 20, 2010, which is incorporated by reference in its entirety herein.

TECHNICAL FIELD

This invention relates generally to the optimization of radiation-treatment leaf-sequence plans and more particularly to the optimization of such plans.

BACKGROUND

The use of radiation to treat medical conditions comprises a known area of prior-art endeavor. For example, radiation therapy comprises an important component of many treatment plans for reducing or eliminating unwanted tumors. Unfortunately, applied radiation does not discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Collimators are often used to restrict and form the radiation-therapy beam. Some collimators have an aperture that can be adjusted in one or more dimension. Adjustable apertures permit, to at least some degree, customization of the radiation-therapy beam's cross section to thereby attempt to better match the requirements of a given target volume. Multi-leaf collimators are an example of such a component. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam.

Many treatment plans provide for exposing the target volume to radiation from a number of different directions. Arc therapy, for example, comprises one such approach. In such a case it often becomes useful or necessary to adjust the multi-leaf collimator to accommodate various differences that occur or accrue when moving the radiation source with respect to the target volume. A radiation-treatment leaf-sequence plan provides information regarding useful or necessary adjustments to the multi-leaf collimator(s) at numerous sequential positions during such a treatment.

Optimizing such a plan can prove challenging. Amongst other things, the radiation target may not be located, shaped, or sized at the time of administering a treatment dosing as was thought to be the case when forming and optimizing the radiation-treatment leaf-sequence plan. To accommodate such a circumstance it is known to plan for dynamic modifications to a given radiation-treatment leaf-sequence plan to thereby attempt to adapt to a patient's presentation at the time of administering the corresponding treatment.

Though helpful to an extent, such a practice sometimes gives rise to one or more new problems. As one example in these regards, a particular planned or theoretically-available modification with respect to the stipulated position of one or more leaves of a multi-leaf collimator may be impossible to achieve due to one or more corresponding physical limitations. For example, a given leaf may simply not have enough time to reach a modified position before the treatment process must continue. This, in turn, can render a planned or accommodated modification theoretically interesting but practically unhelpful.

BRIEF DESCRIPTION OF THE DRAWINGS

The above needs are at least partially met through provision of the method and apparatus pertaining to optimizing a radiation-treatment leaf-sequence plan described in the following detailed description, particularly when studied in conjunction with the drawings, wherein.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments facilitate optimizing a radiation-treatment leaf-sequence plan for use when treating a treatment target in a given patient. This can comprise determining first information regarding physical-movement limitations pertaining to at least one multi-leaf collimator and also determining second information regarding movement of the treatment target with respect to the given patient. These teachings then further provide for, while optimizing the radiation-treatment leaf-sequence plan, constraining individually-planned leaf positions as a function, at least in part, of the first information, the second information, and planned positions of adjacent leaves.

By one approach, the aforementioned first information can comprise information regarding a speed (such as a maximum speed) at which individual leaves of the multi-leaf collimator are able to move during a treatment session. By one approach, the aforementioned second information can comprise information regarding a distance (such as a maximum distance) that one or more parts of the treatment target may possibly move as compared to a presumed position used during the optimizing of the radiation-treatment leaf-sequence plan.

So configured, these teachings can serve to constrain individually-planned leaf positions as a function, at least in part, of planned positions of adjacent leaves. In particular, this can comprise limiting a planned position of a given leaf such that the given leaf is at least likely to be physically capable of being moved, during a treatment session, to a new position that is similar to a position that was planned for another leaf that is adjacent to the given leaf.

By use of these teachings, then, a given radiation-treatment leaf-sequence plan can be modified at a time of need and the modification will, in fact, be physically plausible and hence more likely to preserve the efficacious value of the treatment. In particular, the leaves of the multi-leaf collimator will be able to move to the modified positions as the modifications will be within a range of movement that the leaves can achieve. This, in turn, will help to assure that movements of the treatment target are dutifully and suitably tracked to thereby help to ensure the planned beneficial results of the treatment plan.

These teachings are readily employed in conjunction with existing equipment and hence can serve to greatly leverage the extended viability and useful lifetime of such equipment. These teachings are also highly scalable and can be used with any number of multi-leaf collimators and with any number leaves. In many cases these benefits can be achieved in a highly cost-effective manner.

These and other benefits may become clearer upon making a thorough review and study of the following detailed description. To begin, it may be helpful to first briefly characterize certain aspects of the prior art.

Figure 1:
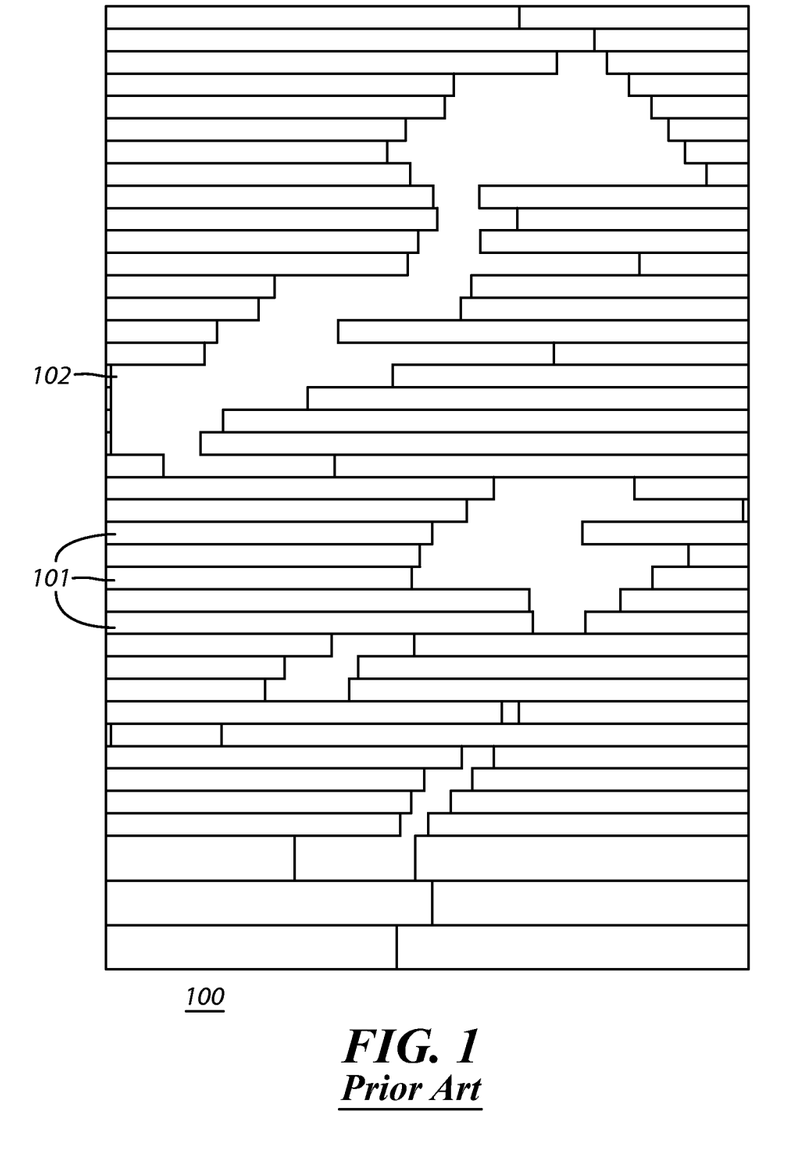
FIG. 1 comprises a front-elevational view as configured in accordance with prior art practice.

FIG. 1 presents an illustrative example of a multi-leaf collimator 100 having a plurality of leaves 101. As shown, each row of the collimator has two such leaves 101 that can be positioned horizontally (in this example, with other possibilities existing in these regards) along the row as desired. More particularly, an opening 102 can be formed by leaving a space between such leaves 101. For the sake of example the multi-leaf collimator 100 in this illustration has a plurality of such openings 102. These openings 102, in turn, comprise apertures through which radiation can pass to reach the intended treatment target (not shown).

During a dynamic treatment process, such as an arc therapy treatment process, the relative positions of these leaves 101 will typically change to accommodate variations in the presentation of the treatment target. As noted above, however, sometimes the treatment target has moved (or has changed in shape or size) as compared to a presumed position that a planning process employed when developing the radiation-treatment leaf-sequence plan. As a very simple example, presume here that the treatment target has moved a few millimeters downwardly. To accommodate this shift in position it would be useful to similarly shift the collimator's aperture(s) 102 downwardly by a similar amount. Unfortunately, one or more physical limitations as tend to characterize a typical multi-leaf collimator can render this difficult or even impossible in some cases.

Figure 2:
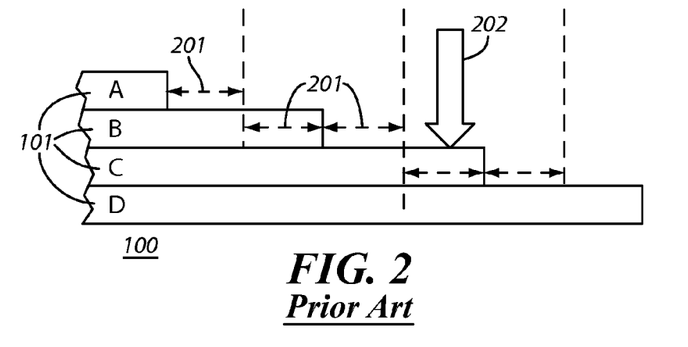
FIG. 2 comprises a front-elevational detail view as configured in accordance with prior art practice.
Figure 3:
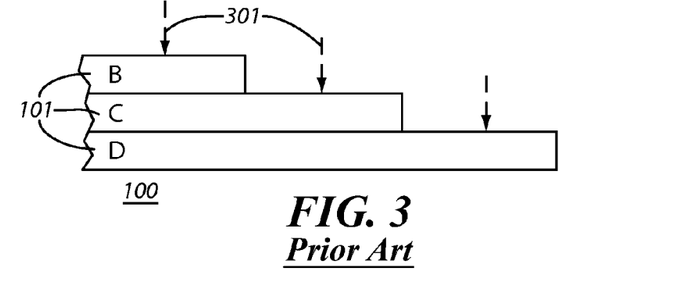
FIG. 3 comprises a front-elevational detail view as configured in accordance with prior art practice.

To exemplify this point in more detail, consider the leaves 101 shown in FIGS. 2 and 3. As noted above, these leaves 101 (denoted here as "A," "B," and so forth) are able to selectively move back and forth. These leaves 101, however, cannot move faster than some maximum speed. In a typical application setting there is also no more than a given amount of time during which such leaves 101 can move before the process must carry on. This combination of limited time and maximum speed means that each leaf 101 can move no more than a maximum distance 201 in either of its directions of motion.

As a result, when there is a need to move a given opening in a given direction 202 (to accommodate, for example, corresponding movement of the treatment target), FIG. 3 represents the maximum change that these leaves 101 can accommodate to try and accomplish the downward shifting of the corresponding aperture. As is also illustrated in FIG. 3, this would result in a horizontal deficiency represented by 301. In sum and substance, the originally-shaped and positioned aperture is now inappropriately located (and also possibly misshapen) because of a need to attempt to match, more or less in real time, movement or other physical changes regarding the treatment target.

Figure 4:
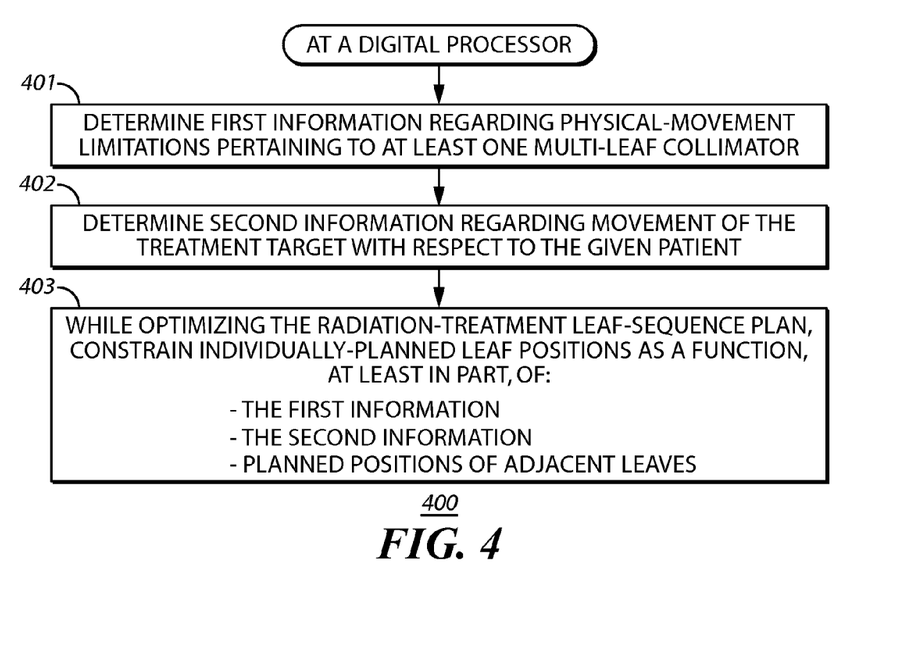
FIG. 4 comprises a flow diagram as configured in accordance with various embodiments of the invention.

Referring now to FIG. 4, an illustrative process 400 that is compatible with many of these teachings will now be presented. This process 400 can be carried out by a control circuit of choice such as a digital processor. The latter may comprise a dedicated platform or may comprise a more generally-programmable platform as desired. In many cases this digital processor can comprise a radiation-treatment leaf-sequence planner (as are known in the art) that has been configured to carry out these teachings.

At step 401 this process 400 determines first information regarding physical-movement limitations pertaining to at least one multi-leaf collimator. (In many application settings there will only be a single multi-leaf collimator. Where the application setting makes use of more than one multi-leaf collimator, however, these teachings will readily accommodate determining this first information for some, or each, of this plurality of multi-leaf collimators.)

This first information can comprise, for example and at least in part, information regarding a speed (such as a maximum or average speed) at which individual leaves of the multi-leaf collimator are able to move during a treatment session. This first information can also comprise, in lieu of the foregoing or in combination therewith, an amount of time that is available for the multi-leaf collimator leaves to move from a beginning position to a concluding position during a treatment session. As yet another example, this first information can comprise a maximum distance that the multi-leaf collimator's leaves are able to move during a treatment session from a beginning position to a concluding position.

These teachings will accommodate determining such information in an automated manner. These teachings will also permit, however, such information to be determined by accessing, for example, a memory having such information already stored therein. In the latter case, for example, an authorized person might have empirically determined the desired information and entered the corresponding value(s) into such a memory.

At step 402 this process 400 also determines second information regarding movement of the treatment target with respect to the given patient. This second information can comprise, for example, a distance (such as a maximum distance) that at least a part of the treatment target may possibly move as compared to a presumed position used during the optimizing of the radiation-treatment leaf-sequence plan. As one illustrative example in these regards, this second information might comprise the information that the treatment target, comprising a tumor, may shrink and may therefore be smaller by up to ten percent than a currently anticipated size. As another illustrative example in these regards, this second information might comprise the information that the treatment target may be lower in the patient's body than expected by up to no more than 3 millimeters.

It is also possible, in combination with the foregoing or in lieu thereof, for this second information to comprise speed information. Illustrative examples in this regard can include, but are certainly not limited to:

That a maximum movement speed of the target is some specified value, such as, for example, 4 mm/s;

That a maximum target movement speed has some specified relationship to another parameter (for example, that the maximum target movement speed is one-half the maximum speed of the collimator leaves);

That a maximum target movement speed is defined as a number ranging from, for example, 0 to 10, where 0 represents a lack of movement and 10 is a fastest anticipated (or possible) movement (Such a parameter need not be tightly bound to a particular physical speed of the target, but could, if desired, be a value that can be used to control the strength of tracking constraint. Such a user definable parameter could pertain to an arbitrary scale with a corresponding constraining level being experimentally determined.).

Step 403 of this process 400 occurs, at least in part, while optimizing a radiation-treatment leaf-sequence plan for a given treatment target as pertains to a given patient. (Radiation-treatment plans are often calculated using an iterative process. Beginning with some initial set of settings, a radiation-treatment planning apparatus iteratively adjusts one or more of those settings and assesses the relative worth of the adjusted plan. An iterative approach such as this is often referred to as "optimizing" the plan (where "optimizing" should not be confused with the idea of identifying an objectively "optimum" plan that is superior to all other possible plans). Various approaches to optimization are known in the art. As optimization in general comprises a well-understood area of endeavor, and as these teachings are not overly sensitive to particular selections in these regards, further elaboration will not be provided here regarding optimization techniques and methodologies.)

More particularly, step 403 provides for constraining individually-planned leaf positions as a function, at least in part, of the aforementioned first information and second information as well as planned positions of adjacent leaves. This can comprise, for example, limiting a planned position of a given leaf such that the given leaf is at least likely to be physically capable of being moved, during a treatment session, to a new position that is similar to a position that was planned for another leaf that is adjacent to the given leaf in order to track movement of the treatment target. (As used herein, this reference to being "physically capable of being moved" refers to the ordinary, every-day leaf-movement performance of a given multi-leaf collimator and its corresponding motive and controlling components and does not include extraordinary measures one could theoretically practice to improve such performance.)

This consideration of "adjacent" leaves can be limited to only leaves that are immediately adjacent to the given leaf if desired. Some application settings may benefit, however, if this notion of being adjacent is extended to include, for example, leaves that are within two or three leaves of the given leaf (or some other range of choice).

Generally speaking, this step 403 can further comprise limiting planned leaf positions such that the given leaves are at least likely to be physically capable of being moved, during a treatment session and in real time, to a new position that is similar to a position that was planned for another leaf that is adjacent to the leaf in question.

So configured, a sequence of leaf positions can be determined that are not only suitable to achieve the intent of a given radiation treatment plan but that can more likely adapt to physical changes with respect to the location/shape/movement of the treatment target in a way that preserves that efficacious intent.

The extent to which such concerns for adjacent leaf positions influences the planned position for a given leaf can be varied as desired. That is to say, such a concern can be made weaker or stronger as may be appropriate to the needs or opportunities that tend to characterize a given application setting. Absolute requirements in these regards, for example, cannot likely be met with precision for all leaves in a one-hundred leaf collimator for each and every aperture configuration in a sequence of multi-leaf collimator settings. The need to comply with such a criterion can be made partially or wholly subservient to other considerations as desired.

Figure 5:
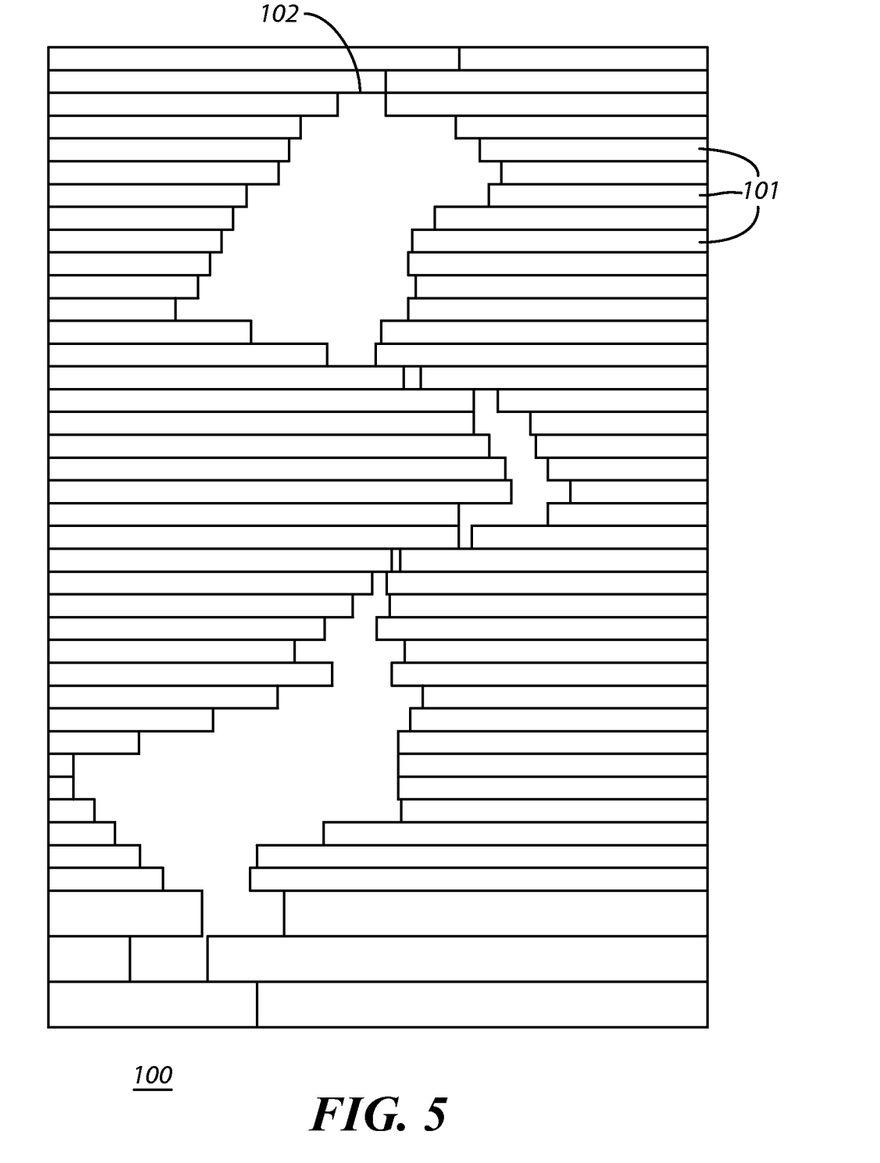
FIG. 5 comprises a front-elevational view as configured in accordance with various embodiments of the invention.
Figure 6:
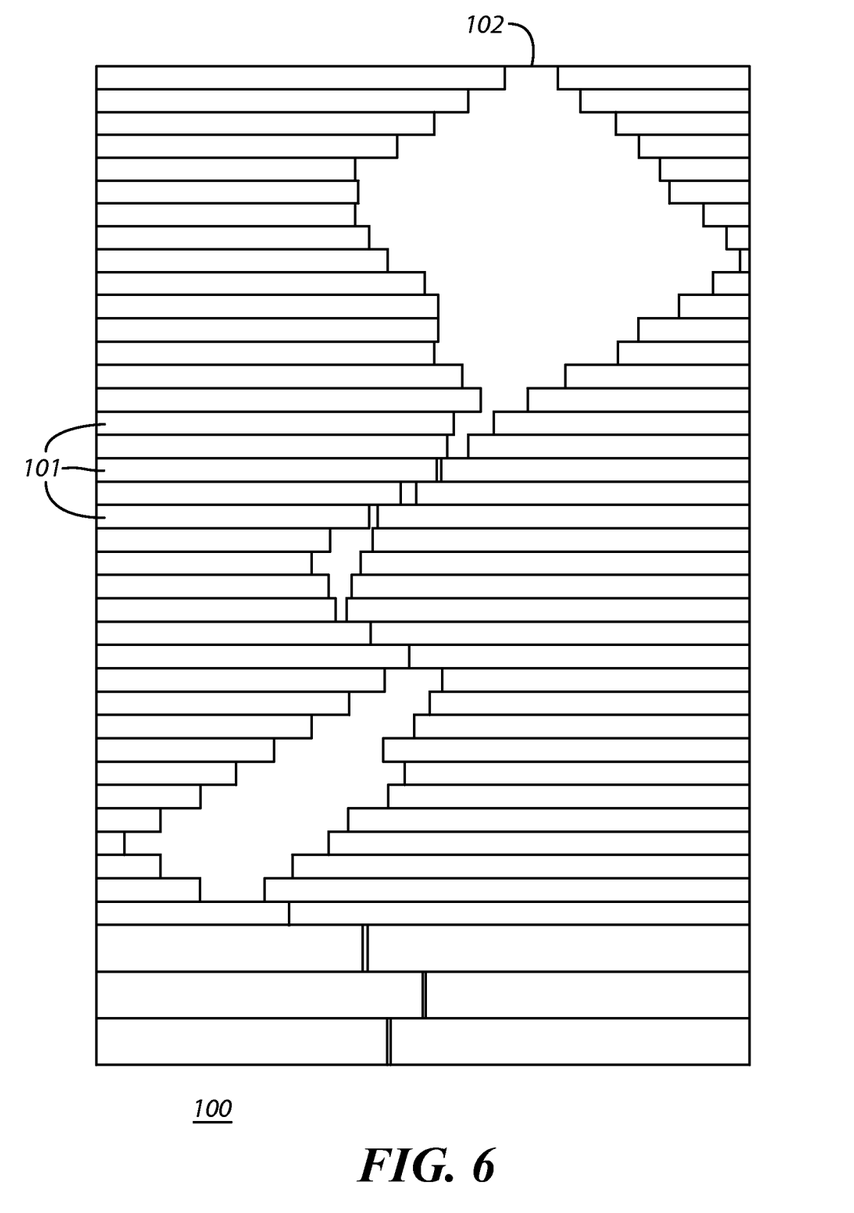
FIG. 6 comprises a front-elevational view as configured in accordance with various embodiments of the invention.

By way of some illustration in these regards, FIG. 5 provides a view of a particular multi-leaf collimator configuration that complies with a weaker tracking constraint in these regards. FIG. 6, in turn, provides a view of a particular multi-leaf collimator configuration that complies instead with a stronger tracking constraint in these regards. Generally speaking, the stronger the tracking constraint, the more likely it will be that the collimator apertures are rounder in shape. Such a tendency is clearly apparent when comparing the somewhat rounder apertures of FIG. 5 (which exemplifies a weak tracking constraint) with the apertures of FIG. 1 (which reflects no tracking constraints whatsoever in these regards) and the even-more rounded apertures of FIG. 6 (which exemplifies a stronger tracking constraint).

Figure 7:
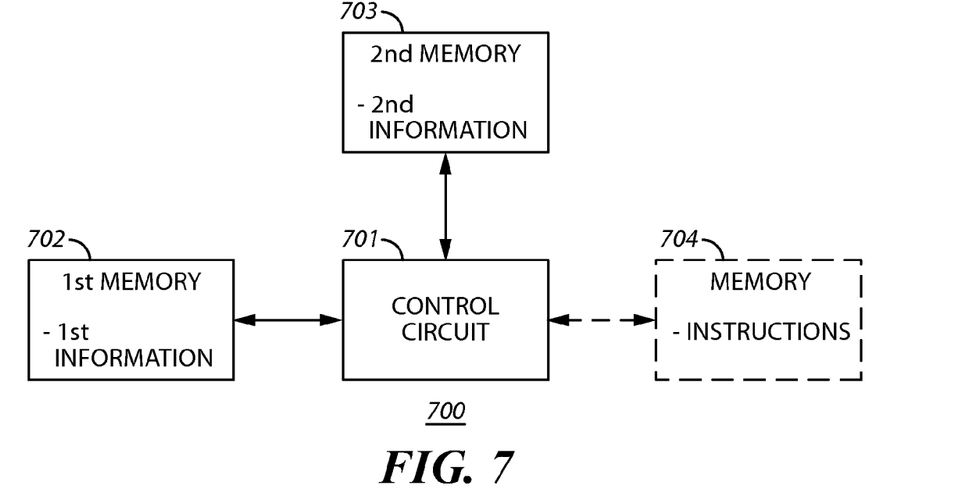
FIG. 7 comprises a block diagram as configured in accordance with various embodiments of the invention.

The above-described processes are readily enabled using any of a wide variety of available and/or readily configured platforms, including partially or wholly programmable platforms as are known in the art or dedicated purpose platforms as may be desired for some applications. Referring now to FIG. 7, an illustrative approach to such a platform 700 will now be provided.

This implementation platform 700 can comprise a control circuit 701 that operably couples to one or more memories. Such a control circuit 701 can comprise a fixed-purpose hard-wired platform or can comprise a partially or wholly programmable platform. All of these architectural options are well known and understood in the art and require no further description here.

By one approach, this control circuit 701 can operably couple to a first memory 702 that contains the aforementioned first information. Similarly, this control circuit 701 can operably couple to a second memory 703 that stores the aforementioned second information. These memories 702 and 703 can of course comprise a single component or can be further parsed over a greater number of digital storage components as desired. These memories 702 and 703 can also be located proximal to the control circuit 701 (by sharing, for example, a same housing, rack, or facility) or can be located remotely from the control circuit 701 (by being located, for example, in another facility, municipality, state, country, or the like).

As noted above, the control circuit 701 may comprise a partially or wholly programmable platform (such as a computer). In such a case, further memory 704 can operably couple thereto (or be a part thereof) and can store the instructions that, when executed by the control circuit, cause the control circuit to carry out one or more of the steps, actions, or functions described herein.

Such an apparatus 700 may be comprised of a plurality of physically distinct elements as is suggested by the illustration shown in FIG. 7. It is also possible, however, to view this illustration as comprising a logical view, in which case one or more of these elements can be enabled and realized via a shared platform.

So configured, one can achieve reliable tracking of a treatment target with respect to the radiation dosing of that target. In particular, these teachings can improve the likelihood that the efficacious and intended benefits of a given radiation-treatment plan that employs one or more multi-leaf collimators will in fact be achieved notwithstanding differences at the time of treatment with respect to the placement, shape, or size of the treatment target as compared to presumptions that were made in these regards at the time of optimizing that radiation-treatment plan.

These teachings are readily employed in conjunction with most if not all optimization approaches practiced today and will no doubt readily accommodate future approaches in these regards as well. Though readily practiced and highly flexible in application, these teachings are also nevertheless economically applied.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. A method to facilitate optimizing a radiation-treatment leaf-sequence plan for use when treating a treatment target in a given patient, comprising:
by a digital processor:
determining first information regarding physical-movement limitations pertaining to at least one multi-leaf collimator;
while optimizing the radiation-treatment leaf-sequence plan, constraining individually-planned leaf positions as a function, at least in part, of the first information and planned positions of at least some adjacent leaves, which adjacent leaves are other than immediately adjacent, such that multi-leaf collimator leaves are at least likely to be physically capable of being moved, during a treatment session, to a new position in order to track changes pertaining to the treatment target, wherein the new position is similar to a position that was planned for the at least some of the adjacent leaves.

2. The method of claim 1 wherein the first information comprises, at least in part, information regarding a speed at which individual leaves of the multi-leaf collimator are able to move during a treatment session.

3. The method of claim 2 wherein the speed comprises a maximum speed at which the individual leaves are able to move during the treatment session.

4. The method of claim 1 wherein the adjacent leaves further include directly adjacent leaves.

5. An apparatus to facilitate optimizing a radiation-treatment leaf-sequence plan for use when treating a treatment target in a given patient, comprising:
a first memory having first information stored therein regarding physical-movement limitations pertaining to at least one multi-leaf collimator;
a control circuit operably coupled to the first memory and configured to, while optimizing the radiation-treatment leaf-sequence plan, constrain individually-planned leaf positions as a function, at least in part, of the first information and planned positions of at least some adjacent leaves, which adjacent leaves are other than immediately adjacent, such that multi-leaf collimator leaves are at least likely to be physically capable of being moved, during a treatment session, to a new position in order to track changes pertaining to the treatment target, wherein the new position is similar to a position that was planned for the at least some of the adjacent leaves.

6. The apparatus of claim 5 wherein the first information comprises, at least in part, information regarding a speed at which individual leaves of the multi-leaf collimator are able to move during a treatment session.

7. The method of claim 6 wherein the speed comprises a maximum speed at which the individual leaves are able to move during the treatment session.

8. The apparatus of claim 5 wherein the adjacent leaves further include directly adjacent leaves.

9. The apparatus of claim 5 wherein the adjacent leaves further include directly adjacent leaves.

10. A method to facilitate optimizing a radiation-treatment plan for use when treating a treatment target in a given patient, which radiation-treatment plan presumes use of at least one multi-leaf collimator having a plurality of individually-movable leaves, comprising:
by a digital processor:
determining first information regarding physical-movement limitations pertaining to the multi-leaf collimator;
while optimizing the radiation-treatment plan, constraining individually-planned leaf positions as a function, at least in part, of the first information and planned positions of at least some adjacent leaves, which adjacent leaves are other than immediately adjacent, such that the multi-leaf collimator leaves are at least likely to be physically capable of being moved, during a treatment session, to a new position in order to track changes pertaining to the treatment target, wherein the new position is similar to a position that was planned for the at least some of the adjacent leaves.

* * * * *

UNITED STATES PATENT AND TRADEMARK OFFICE
CERTIFICATE OF CORRECTION

PATENT NO. : 9,138,598 B2
APPLICATION NO. : 13/630374
DATED : September 22, 2015
INVENTOR(S) : Janne Nord et al.

Page 1 of 1

It is certified that error appears in the above-identified patent and that said Letters Patent is hereby corrected as shown below:

IN THE CLAIMS:

In Claim 7, column 8, line 29, delete "method" and insert --apparatus--.

Signed and Sealed this
Fifteenth Day of March, 2016

Michelle K. Lee
*Director of the United States Patent and Trademark Office*